United States Patent
Fennell et al.

[11] Patent Number: 5,670,707
[45] Date of Patent: Sep. 23, 1997

[54] CALIBRATION METHOD FOR A CHROMATOGRAPHY COLUMN

[75] Inventors: Martin John Fennell, Fairfield; Craig Clark Hodges, Walnut Creek, both of Calif.

[73] Assignee: Varian Associates, Inc., Palo Alto, Calif.

[21] Appl. No.: 743,450

[22] Filed: Nov. 1, 1996

[51] Int. Cl.$^6$ .................................................. G01N 30/10
[52] U.S. Cl. .................................................. 73/1 G
[58] Field of Search .................. 73/1 R, 1 G, 23.36, 73/61.52, 61.57

[56] References Cited

U.S. PATENT DOCUMENTS 5,339,673  8/1994  Nakagawa et al. .................. 73/23.36

Primary Examiner—Robert Raevis
Attorney, Agent, or Firm—Gerald M. Fisher

[57] ABSTRACT

A chromatography system and method employing an empirical method for determining the ratio $$\frac{d^4}{L}$$

for a chromatography column with improved accuracy by establishing experimental conditions for at least one of the parameters of temperature, pressure and flow and measuring the other parameters and calculating the ratio $$\frac{d^4}{L}$$

using the Poiseville equation for a chromatography column.

8 Claims, 4 Drawing Sheets

5,670,707

CALIBRATION METHOD FOR A CHROMATOGRAPHY COLUMN

FIELD OF THE INVENTION

The present invention relates to chromatography and more particularly to a method of accurately determining characterizing parameters for chromatography columns and for improving chromatography repeatability.

BACKGROUND OF THE INVENTION

Chromatography is a method for separating chemical mixtures into their components.

In chromatographic analysis an unknown mixture of chemicals is caused to flow into contact with a retentive media. The various portions of the mixture are detained by the media by differing amounts of time so that separations of the mixture are enabled. In the branch of chromatography known as gas chromatography, typically a supply of an inert gas called a carrier gas is continuously flowed through a device called a chromatography column. In analytical chromatography the most common form of column is a very long hollow capillary tube. The interior walls of the capillary tube provide the retentive surface which interaction provides separation of the chemical components. Generally, the interior tube walls are chemically treated to enhance the separation. The term chromatographic column also includes tubes having packed particles providing a porous medium to detain the portions of a mixture. The primary separation mechanism in these columns is derived from the interactions between the surface of the particles and the flowing mixture. Typically, the mixture to be analyzed is loaded in liquid form into an injector where it is rapidly heated into the vapor state. The injector also provides a continuous flow of carrier gas into the column and when the sample unknown is vaporized it is introduced into the head of the column by the injector as a slug of gas. The slug is forced through the column by the pressure of the carrier gas and as the gases travel down the column, the components of the unknown sample separate into bands of like materials which like materials progress down the column at a common rate. Accordingly, at the output of the column, the various components leave the column in small bands separated in time. The time which the components travel through the column is a characteristic of the particular column, the column temperature, the carrier gas flow rate and the chemical of the component. Accordingly, a column can be calibrated so that the retention time of a chemical in the column is an unambiguous, qualitative identification of the chemical. Quantitative analysis of a sample is also enabled by determining the volumes of sample of the various bands and by integrating the signal of the detector at the exit of a column for each portion of the mixture.

It is known to increase the column temperature or other parameters, such as carrier gas flow rate, during a chromatography run primarily to shorten the time to perform the separation or to improve the resolution of the separation. However, the effects of varying a parameter introduces many complexities. For example, it is known in the prior art to perform temperature programing, i.e. to vary the temperature during a run and to employ computed changes in viscosity as a function of temperature to control either the column input pressure or the column mass flow rate. However, the equations which relate temperature, flow and pressure, also require an input of data about the column. For a capillary column, for example, to calculate the mass flow rate in a column as a function of the input pressure requires exact knowledge of the internal diameter and length of the column. Although the approximate length and internal diameter are usually easily determined, it is much more difficult to determine the exact dimensions. Use of incorrect values for these parameters leads to significant errors in the calculated flow rates. The manufacturer of a column usually provides approximate dimension parameters, but these are modified by the installation and use.

The most common prior art technique for calibrating a column involves performing a chromatography run using a reference chemical which is different from the carrier gas but which also has no chemical interaction with the column and measuring the retention time of the reference gas. From known formulas, the length and internal column diameter can then be calculated. However, this technique involves injection processes subject to mechanical and human error. In addition, it is not readily known which chemicals have no reaction with a particular capillary column. Furthermore, these prior calibration processes are very time consuming and difficult to repeat exactly. Another source of error arises in the calculations because it is frequently assumed that the outlet pressure of the column is at atmospheric pressure. In fact, it is generally necessary to determine the exact pressure drop between the end of the column and the atmosphere because apparatus and fittings can cause significant back pressure which significantly effects the calibration.

SUMMARY OF THE INVENTION

It is an object of the invention to provide a method to improve the accuracy of flow control in a chromatography system by improving the accuracy of calibration of the ratio of diameter/length of the chromatography column. It is a further object to provide alternative methods to determine the $$\frac{d^4}{L}$$

ratio of chromatography columns.

It is still a further object to provide improved chromatography control systems employing column parameter ratio calibration measurements which compensate for inaccuracies in column temperature measurements.

ratio in the pressure control computer.

Figure 4:
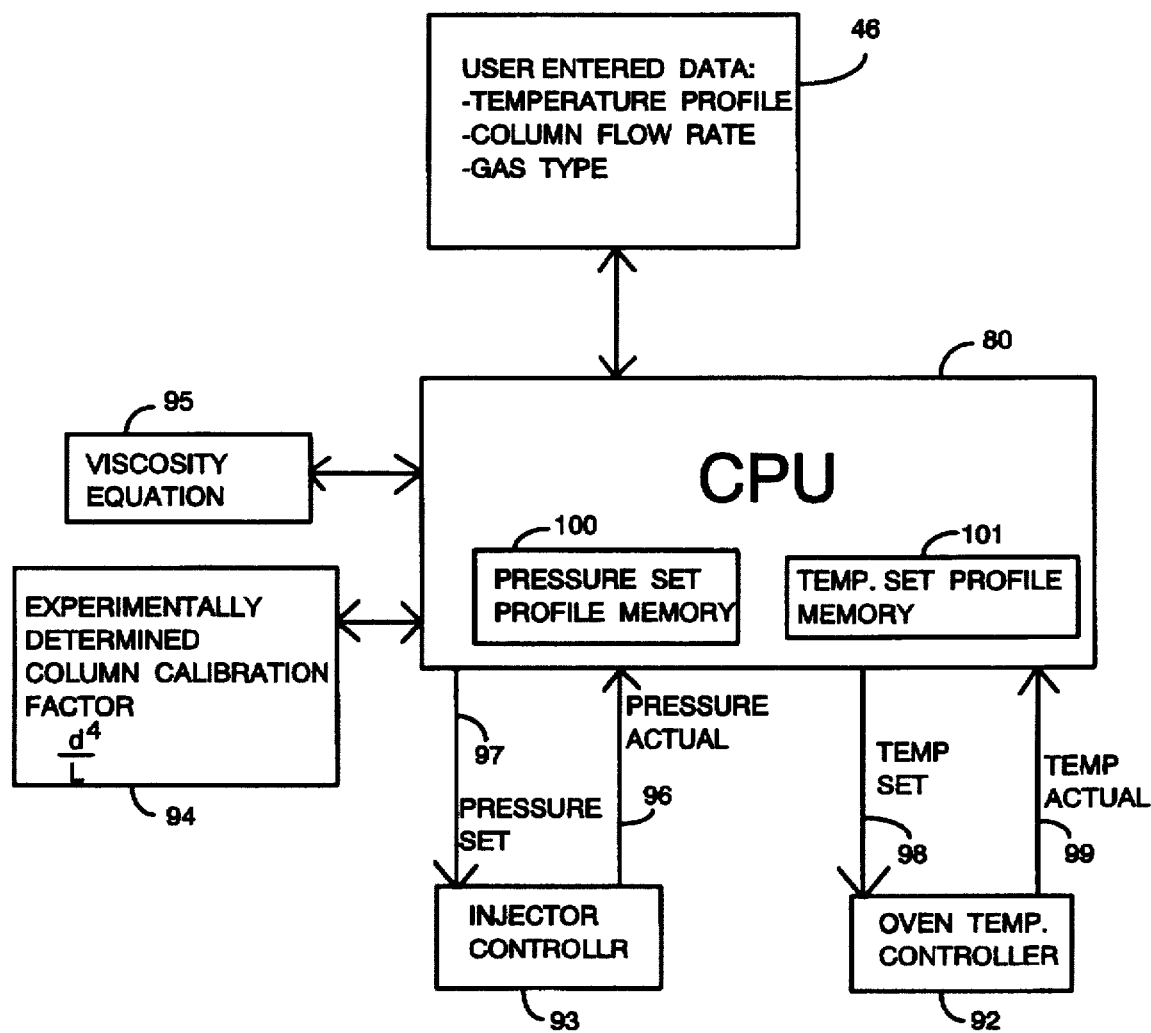

FIG. 4 is a block diagram of the preferred chromatography control system.

DETAILED DESCRIPTION OF THE INVENTION

Figure 1:
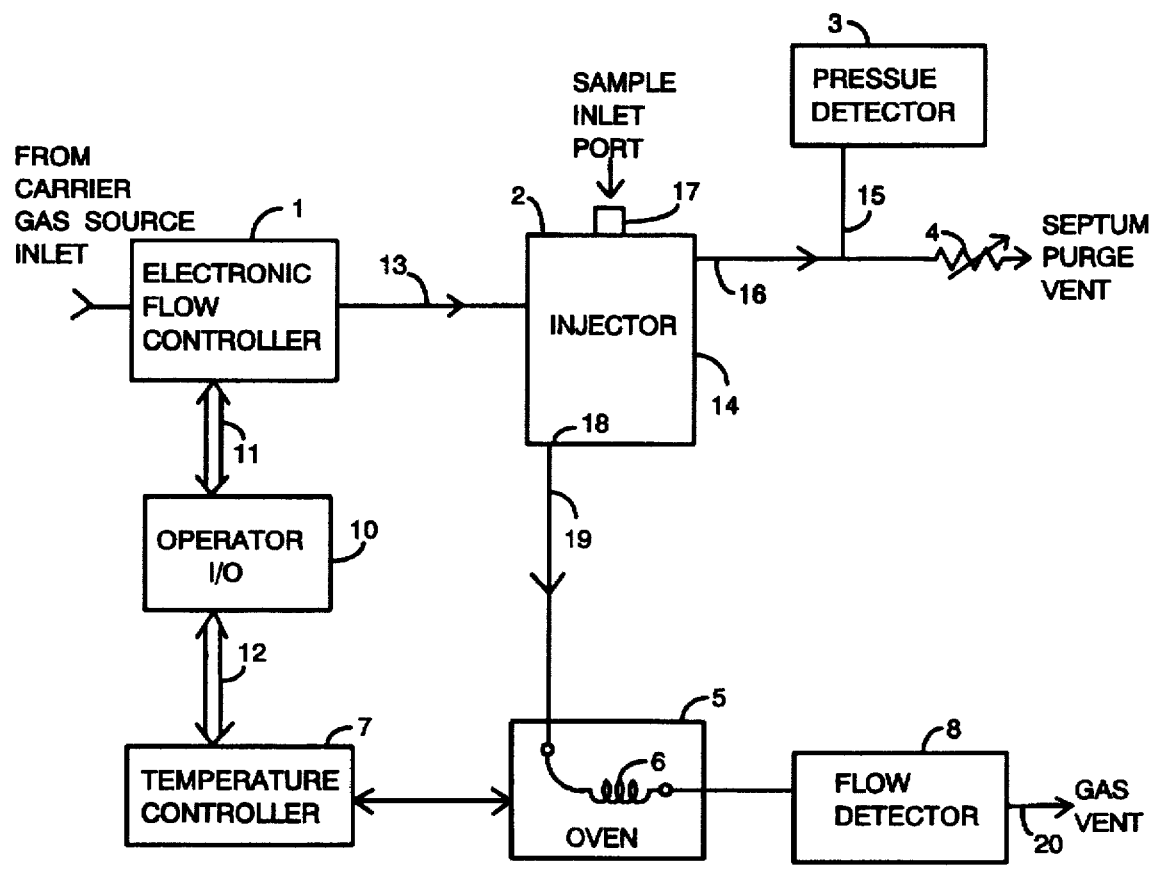
FIG. 1 is a schematic of the equipment configuration for column calibration.
Figure 3:
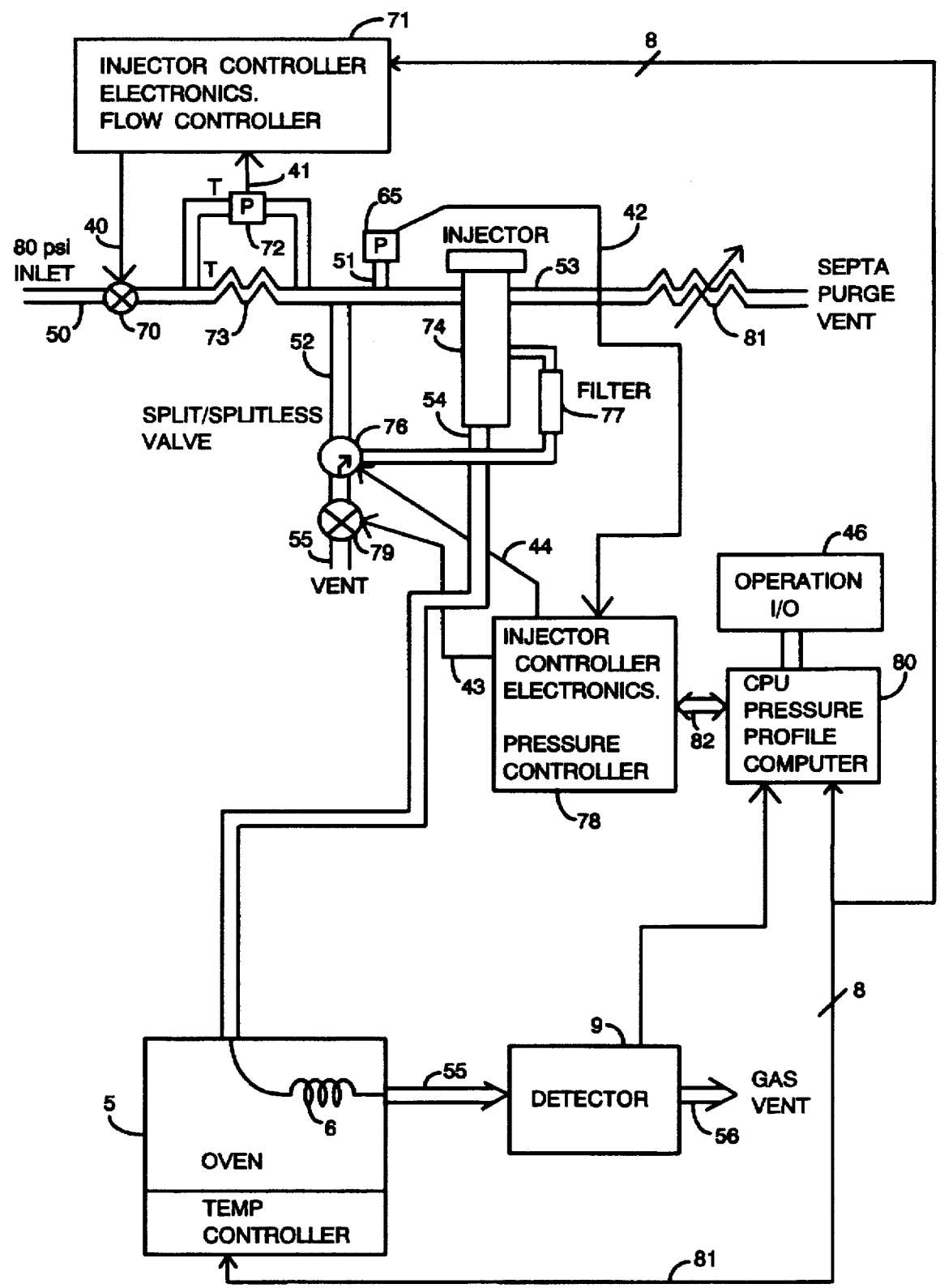
FIG. 3 is a schematic of the computerized flow controller employing the calibrated value of $$\frac{d^4}{L}$$

To determine the ratio $$\frac{d^4}{L}$$

of a column with the accuracy required for fine flow control, with reference to FIG. 1, the column 6 is installed in a temperature controlled oven 5. The equipment necessary for determining the ratio further includes an electronic flow controller 1 under digital control from an operator input/output device 10 such as a key board. The electronic flow controller 1 is connected to receive the carrier gas from a pressure source. For best calibration, the carrier gas should be the same as the carrier gas which is to be used in the tests with the chromatography column even though the calibration ratio $$\frac{d^4}{L}$$

should be the same for different carrier gases. The flow controller 1 is connected via flow line 13 to an injector 2. The injector is preferably the same type, and even more preferably, the identical injector with which the column is to be used. Injectors are well known devices which are designed to receive a liquid sample to be analyzed which enable vaporization of the liquid sample and which ideally enable a slug of the vaporized sample to be introduced into the head of the column by the carrier gases and for the vaporized sample to be moved through the column by the flow of the carrier gas. The details of the injector are not a part of this invention but it is essential to appreciate that the injector employs a sample inlet port 17, comprising a septum (not shown) through which a syringe needle can be passed to deposit the liquid sample where it is vaporized. Typically an injector 14 directs a potion of its inlet gas 13 into a septum purge vent 16. It is generally preferred to purge and vent the gases which leak from the septum material because those gases would mask and/or interfere with the separation of the gases of the unknown sample. Inlet systems such as injectors are described in Chapter 4 of the well known text book entitled *Gas Chromatography with Glass Capillary Columns* by Walter Jennings, Acad. Press, Inc., 1980; said Chapter 4 being hereby incorporated by reference. A pressure detector 3 is coupled to the purge outlet vent 16 or, alternatively, to the inlet 13. By reason of the design of the injector 14, the pressure at the inlet 13 and outlets 16 and 18 are equal. Accordingly, pressure measured at the pressure detector 3 is equal to the pressure at the inlet to the column 6 except for a pressure drop in the tubing 19. Alternatively, the column 6 can be connected directedly to the injector 14 or if tubing 19 is employed it has a large diameter and is very short so that any pressure drop therein is negligible for the purposes of this application. Preferrably the electronic flow controller 1 which is employed is pre-calibrated so that the output 41 of pressure meter 72, FIG. 3, is a measure of the flow from valve 70. Accordingly, valve 70 controls the flow from the supply 50 and valve 79 controls the head pressure at 13/15/51. Alternatively, a flow detector 8 can be used to measure the actual gas flow rate in the column 6 because all gas in the column flows through flow detector 8 and then to vent line 20.

There is a well known formula called the Poiseuille equation relating the gas flow rate in a column to a number of parameters. This equation is:

$$Q = \frac{\pi}{256} \frac{d^4}{L} \rho_s \frac{T_s}{T_c} \frac{(P_i)^2 - (P_o)^2}{P_s} \frac{1}{U_{T_c}} \quad [1]$$

where

Q=column mass flow rate
$U_{Tc}$=gas viscosity at column temperature
Tc=column temperature (Kelvin)
Ts=standard temperature (Kelvin)
ps=density of gas at standard temperature and pressure
d=column internal diameter
L=column length
Pi=inlet pressure (PSIA)
Po=outlet pressure (PSIA)
Ps=standard ambient pressure(PSIA)
$\pi$=3.141592654

Accordingly, it is possible to determine the ratio $$\frac{d^4}{L}$$

experimentally by creating appropriate experimental conditions for the column and by recording data regarding column flow rate and column inlet pressure and by performing appropriate calculations. There are several alternative procedures which can be established which theoretically enable the solution of $$\frac{d^4}{L}.$$

However, due to the fact that as the injector inlet pressure changes, small injector leaks change, the calibration technique which is based on a constant column inlet pressure as depicted hereinafter is the preferred method.

More specifically, if one creates two sets of conditions at two different temperatures but retains the column inlet pressure Pi and outlet pressure Po the same for both sets, the equation [1] can be solved as two simultaneous equations at two different temperatures. This procedure will result in two flow rates Q1 and Q2 which can be determined experimentally. Using the differences between the two flows, the ratio $$\frac{d^4}{L}$$

can be determined by solving the equation:

$$\frac{d^4}{L} = \frac{256 \, dQ T_{c1} P_s U_{Tc1} T_{c2} U_{Tc2}}{(\pi)(\rho_s)(T_s)[(P_1)^2 - (P_o)^2][(T_{c2})(U_{Tc2}) - (T_{c1})(U_{Tc1})]} \quad [2]$$

The derivation of equation [2] is depicted below.

$$Q1 = \frac{\pi d^4}{256 L} \rho_s \frac{T_s}{T_{c1}} \frac{(P_i)^2 - (P_o)^2}{P_s} \frac{1}{U_{Tc1}} \quad [3]$$

$$Q_2 = \frac{\pi}{256} \frac{d^4}{L} \rho_s \frac{T_s(p_i)^2 - (P_o)^2}{P_s} \frac{1}{U_{Tc2}} \quad [4]$$

let dQ=change in flow rate between temperature 1 and temperature 2 for constant input pressure [5]

therefore:

$$Q2 = Q1 - dQ$$

then substitute [6] into [4], then [3] into [4] and solve for $$\frac{d^4}{L}$$

$$\frac{d^4}{L} = \frac{256 \, dQ T_{c1} P_s U_{Tc1} T_{c2} U_{Tc2}}{(\pi)(\rho_s)(T_s)[(P_1)^2 - (P_o)^2)][(T_{c2})(U_{Tc2}) - (T_{c1})(U_{Tc1})]} \quad [7]$$

Figure 2:
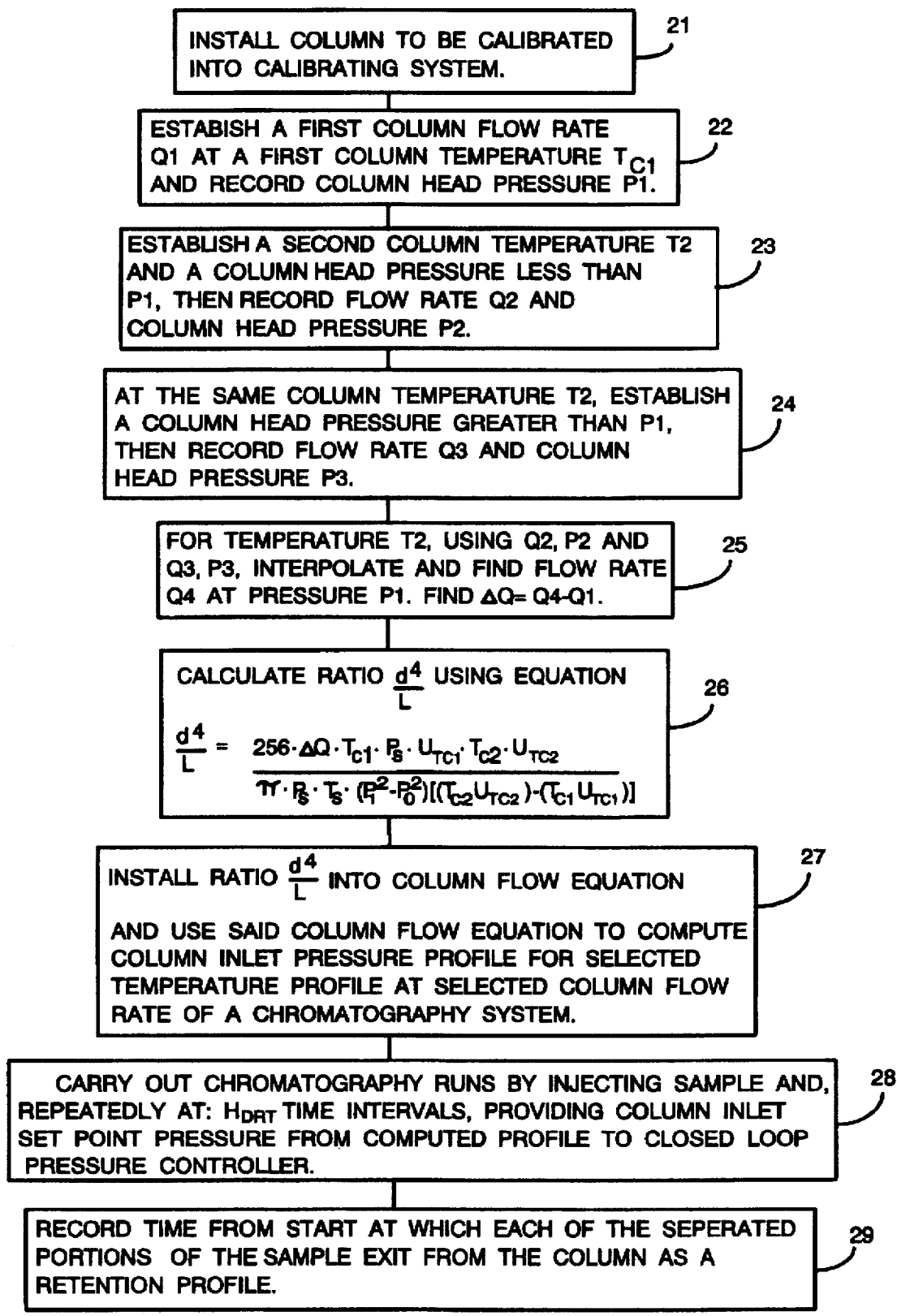
FIG. 2 is a schematic of the preferred flow diagram of the preferred calibration method.

Referring to FIG. 2, the preferred constant pressure method of calibration is set forth. First, in step 21, the column to be calibrated is installed into the oven of the calibrating system. Next, in step 22, establish a first injector flow rate Q1 at a first column temperature TC1 and record the column head pressure P1 when the temperature TC1 is stable.

Next, change the temperature in the oven to a second temperature TC2 for step 23, and establish a column head pressure P2 where P2<P1 and store/record flow rate Q2.

At the same temperature TC2, in step 24, establish a column head pressure P3, where P3>P1, and store/record flow rate Q3.

Interpolate linearly using Q2, P2 as one set of points and Q3, P3 as a second set of points, and find Q4 at pressure P1. Now find ΔQ=Q4−Q1

Next calculate $$\frac{d^4}{L}$$

using the data obtained here and substitute in equation [2].

Finally, install automatically or manually, the value of the ratio $$\frac{d^4}{L}$$

determined by equation [2] into the memory of computer 80 (FIG. 3 and FIG. 4) for use in computing the pressure set point for the head of the column to achieve the column mass flow rate selected by the operator via the I/O control 46. The installation step could be manual through the operator control 46 or automatically via a calibration program carried out by the computer 80.

If the flow controller 1 is a very high gain controller with a fine resolution, it would be possible to simplify this procedure by simply skipping the interpolation step 24 of FIG. 2 and establishing ΔQ=Q$_2$−Q$_1$ and then, without any other changes, carrying out the remainder of the method of FIG. 2.

There are several alternatives to the preferred method of FIG. 2 for determination of $$\frac{d^4}{L}$$

ratio. For example, data can be obtained from n multipoints at different temperatures, recording both flow rate and corresponding pressure and calculating $$\frac{d^4}{L}$$

for each set of points (Qn, Pn) for each temperature and averaging $$\frac{d^4}{L}$$

for all the various temperatures. Another alternative is at each temperature, to obtain n data points by maintaining the flow constant Qn and recording the corresponding Pn and calculating $$\frac{d^4}{L}$$

with the equations and averaging $$\frac{d^4}{L}.$$

However, each of these non-preferred methods have the disadvantage that different column inlet pressure induce changes both in the septum flow rate in the injector and changes in the injector leaks, which changes and leaks must be compensated or they will introduce error in the results.

The method of this invention for experimentally determining the ratio $$\frac{d^4}{L}$$

is both more accurate and much faster than the prior art procedure of performing hold-up time measurements with non-retained chemicals. An additional advantage is that method of this invention can be fully automated, which will eliminate human error and permit re-calibration at set intervals.

A further advantage of this technique is that if the column calibration is carried out using the same chromatography system which it is to be later used with the column that the process will automatically compensate for error between requested and established column oven temperatures during calibration. Since the calibration is performed using the temperatures measured and established by the chromatography system, any inaccuracy between actual column temperature and the column temperature reading will cause a corresponding change in the constant $$\frac{d^4}{L}.$$

Accordingly, subsequent use of the $$\frac{d^4}{L}$$

ratio will tend to be correct for the temperature employed. Similarly, again assuming that the using system is the same as the calibration system, the value of $$\frac{d^4}{L}$$

will also include a compensation for an error based on any back pressure differential between the column output and atmospheric pressure due to the presence of detectors and other devices restricting the output flow.

With respect to FIG.3, a schematic of a typical computerized chromatography system is shown which system can be employed both for calibration of a column and to employ the column in many types of chromatography experiments.

In operation, carrier gas enters the system 50 at relatively high pressure such as 40–100 psig at inlet 50 and then passes through a proportional control valve 70 and flow restrictor 73. As gas flows through the restrictor 73, it generates a pressure drop which is detected by sensor 72. An electronic control circuit 71 forms a closed loop controller by adjusting the drive voltage 40 to valve 70 in response to signal 41. The Central Processing Unit 80 provides control signal adjustment in response to a user's request 46 for a specified flow rate. The CPU 80 also continuously receives the column temperature information on bus 81 and accordingly, by using the known temperature 7 and pressure 42, the CPU is able to compute a temperature correction signal and pressure set point which is sent to the pressure controller 78. The pressure controller 78 adjusts the vent 79 to control the head pressure 51. Electronic flow controller 71 is corrected for maintaining desired mass flow rate by the computer 80. The calibration data for this compensation which relates pressure 51 and pressure signal 41 is stored in the memory of computer 80.

FIG. 3 illustrates an injector 74 having a split mode and a splitless mode of operation. In the split mode, the three way diverting valve 76 is switched responsive to CPU control 44 so that gas can pass through the filter 77 and vent via proportional control valve 79. A pressure signal 42 is generated by pressure transducer 65 and represents the column head inlet pressure 51. Pressure controller 78 is responsive to pressure sensor 65, and to the CPU 80. The CPU performs the column flow equation computations to provide the pressure set point on bus 82 to the pressure controller 78. The pressure controller sends the control signal 43 to the proportional valve 79 and thereby controls the pressure at the column head and thereby the flow through the column 6. In the splitless mode, the valve 76 is de-energized and the line 52 is directly connected to the proportional controller. Control of the injector pressure is still carried out in the same way by the pressure control computer 78. The split flow injector is used to split off a small portion of a sample for insertion of only a small slug of unknown sample for sweeping into the column by the carrier gas. Generally, after injection, the splitter is de-energized and the injector flow rate is reduced to save carrier gas.

With reference to FIG. 4, the general block diagram of the preferred chromatography system is further explained. The CPU 80 is programmed and set up to solve the Poiseville equation [1] responsive to the User Entered Data 46, the viscosity equation 95 for the given gas and the $$\frac{d^4}{L}$$

parameter 94. Based on the above data, the CPU calculates and stores a pressure set profile in memory 100 and a temperature set profile in memory 101 for the run. As a function of time, the appropriate set points 97 and 98 for pressure and temperature respectively are output from the CPU to their respective pressure and temperature controllers 93 and 92. The controllers employ electronic feedback controls to establish the requested set points and also feedback the actual measured values of actual column inlet pressure 36 and actual oven measured temperature 92 to the CPU.

It is understood that the column flow rate could also be established by selecting viscosity data from a table for specific gases and temperatures and performing the set point column head pressure on the fly. Either approach requires an accurately calibrated $$\frac{d^4}{L}$$

ratio in order to achieve repeatable results based on Poiseville equation computations.

It is not the intent to limit the scope of the invention to the preferred embodiment, but rather the scope of the invention should be construed in view of the claims. With this in mind,

What is claimed is:

1. A method for performing chromatography, said method comprising:

(a) installing a chromatography column to be calibrated into a computer controlled chromatography system, said computer controlled chromatography system including an injector and memory and temperature controller and flow controller means to establish and maintain both selected column temperature and selected fluid flow rate in said column and further including a pressure detector for providing a reading of the pressure at the head of said column, and a flow controller meter for providing said injector with fluid flow rate adjustments;

(b) determining the ratio $$\frac{d^4}{L}$$

of said column, said step of determining the ratio including (i) establishing a first stable temperature TC1 in said column, and establishing a first column head pressure P1 and recording the first column flow Q1;

(ii) carrying out said step (i) n times;

(iii) computing an average $$\frac{d^4}{L}$$

for said column at said first temperature TC1 by solving for $$\frac{d^4}{L}$$

the column flow equation and inserting said values P1, Q1 and Pn, Qn into said equation as follows $$\left[\frac{d^4}{L}\right]_1 = \frac{Q_1}{\frac{\pi}{256} P_s \frac{T_s}{T_{c1}} \frac{[(P_1)^2 - (P_0)^2]}{P_s} \frac{1}{U_{T_{c1}}}}$$

and $$\left[\frac{d^4}{L}\right]_n = \frac{Q_n}{\frac{\pi}{256} P_s \frac{T_s}{T_{c1}} \frac{[(P_n)^2 - (P_0)^2]}{P_s} \frac{1}{U_{T_{c1}}}}$$

where n is a positive, real integer greater than zero, (iv) determining the average $$\left[\frac{d^4}{L}\right]_{ave} = \frac{\left(\frac{d_4}{L}\right)_1 + \cdots + \left(\frac{d_4}{L}\right)_n}{(n)}$$

(c) installing said $$\left(\frac{d^4}{L}\right)_{ave}$$

into said memory of said computer controlled chromatography system where

Q=column mass flow rate
UTC=gas viscosity at specified column temperature
Tc=column temperature (Kelvin)
Ts=standard temperature (Kelvin)
ps=density of carrier gas at standard temperature and pressure
d=column internal diameter
L=column length
Pi=inlet pressure (PSIA)
Po=outlet pressure (PSIA)
Ps=standard ambient pressure(PSIA)
π=3.141592654
Tc1=column temperature in step i
P1=column inlet head pressure in step i
Tc2=second column temperature
P2&Pn=column inlet head pressure in steps (ii) and (iii) respectively; and (d) carrying out chromatography runs by injected sample into said column and employing said calibrated $$\left(\frac{d^4}{L}\right)_{ave}$$

in providing column inlet set point pressures.

2. The method of claim 1 including the steps of (e)(i) establishing a second temperature Tc2 in said column, and establishing at said second temperature a first column head pressure $P1_{Tc2}$ and recording said first column flow rate at said second temperature $Q1_{Tc2}$; and then (ii) establishing at said second temperature Tc2, j sets of column head pressure values $Pj_{Tc2}$ and recording corresponding column flow rates $Qj_{Tc2}$; and (f) calculating the average ratio for said second temperature Tc2 by inserting the sets of data for pressure and flow form steps e(i) and e(ii), where Pjk and Qjk are the jth points in the set of data at the kth temperature field $$\left[\frac{d^4}{L}\right]_{Tck} = \sum_{j=1}^{n} \frac{Q_j \times \frac{1}{n}}{\frac{\pi}{256} \rho_s \frac{T_s}{T_{ck}} \frac{[(P_j)^2 - (P_o)^2]}{P_s} \frac{1}{U_{Tck}}}$$

where
j=set number
k=temperature field number, and (g) obtaining multitemperature point average ratio by calculating $$\left[\frac{d^4}{L}\right]_{ave} = \frac{\left(\frac{d^4}{L}\right)_{Tc1} + \ldots \left(\frac{d^4}{L}\right)_{Tck}}{(k)}$$

where k is a positive real integer greater than zero.

3. The method of claim 2 where k>1.

4. The method of claim 1 for controlling the column fluid flow rates in a calibrated, chromatography column, comprising:

(a) causing a digital computer to solve the flow equation $$Q = \frac{\pi}{256} \frac{d^4}{L} \rho_s \frac{T_s}{T_c} \frac{(P_i)^2 - (P_o)^2}{P_s} \frac{1}{U_{Tc}}$$

(b) causing said digital computer to compute a pressure set-point profile to control said column inlet pressure Pi according to the solution of said flow equation of step (a) to maintain said mass flow rate Q constant irrespective of changes in column temperature Tc;

(c) causing said digital computer to provide to an electronic pressure servo controller repeatedly, at short intervals, new pressure set-points, said electronic pressure servo controller establishing and maintaining said pressure set-points in response to said digital computer.

5. A method for performing chromatography, said method comprising:

installing a chromatography column to be calibrated into a computer controlled chromatography system, said computer controlled chromatography system including means to establish and maintain both selected column temperatures and fluid flow rates in said column and further including, a pressure detector for providing a reading of the pressure at the head of said column and a flow rate meter for providing column fluid flow rate measurements;

experimentally determining the ratio $$\frac{d^4}{L}$$

of said column, said step of determining the ratio including the steps of (a) establishing a first stable temperature TC1 in said column and a first flow rate Q1 in said column and storing the corresponding pressure P1 at the head of said column;

(b) establishing a second stable temperature TC2 in said column and a second column head pressure P2, where P2>P1 and storing the corresponding second column flow rate Q2 in said column;

(c) establishing at said second stable temperature TC2 in said column a third column head pressure P3, where P3<P1 and storing the third column flow rate Q3 in said column;

(d) using said points Q2, P2 and Q3, P3 determined from steps (b) and (c) respectively, linearly interpolate to determine a column flow rate Q4 at head pressure P1 for said column temperature TC2;

(e) determine ΔQ=Q4−Q1 and calculate the ratio $$\frac{d^4}{L}$$

using the equation $$\frac{d^4}{L} = \frac{256 \Delta Q T_{c1} P_s U_{Tc1} T_{c2} U_{Tc2}}{(\pi)(\rho_s)(T_s)[(P_1)^2 - (P_o)^2][(T_{c2})(U_{Tc2}) - (T_{c1})(U_{Tc1})]}$$

where
Q=column mass flow rate

UTC=gas viscosity at specified column temperature
Tc=column temperatures (Kelvin)
Ts=standard temperature (Kelvin)
ps=density of carrier gas at standard temperature and pressure
d=column internal diameter
L=column length
Pi=inlet pressure (PSIA)
Po=outlet pressure (PSIA)
Ps=standard ambient pressure (PSIA)
π=3.141592654
Tc1=column temperature in step a
P1=column inlet head pressure in step a
Tc2=column temperature in steps (b) and (c)
P2&P3=column inlet head pressure in steps (b) and (c) respectively
(f) installing said $$\frac{d^4}{L}$$

ratio into said computer controlled system; and (g) carrying out chromatography runs by injecting samples and by setting set point pressures calculated using said $$\frac{d^4}{L}$$

ratio determined in step (e) above.

6. A method for performing chromatography, said method comprising:

installing said chromatography column to be calibrated into a computer controlled chromatography system, including means to establish and maintain both selected column temperature and fluid flow rate in said column and further including a pressure detector for providing a reading of the pressure at the head of said column and a means for providing column fluid flow rate measurements; experimentally determining the ratio $$\frac{d^4}{L}$$

of said column, said step of experimentally determining said $$\frac{d^4}{L}$$

ratio including the steps of:

(a) establishing a first stable flow Q1 in said column and a first temperature Tc1 in said column and recording said pressure P1 at the head of said column;

(b) establishing a second stable flow Q2 in said column at a second temperature Tc2 in said column said Q2>Q1, and recording said corresponding pressure P2 at the head of said column;

(c) establish a third stable flow Q3 in said column, at said second temperature Tc2 said Q3<Q1, and recording said second corresponding pressure P3 at the head of said column;

(d) using said points Q2, P2 and Q3, P3 determined from steps (b) and (c) respectively, linearly interpolate to determine a column flow rate Q4 at head pressure P1 for said column temperature Tc2;

(e) determine ΔQ=Q4-Q1 and calculate the ratio $$\frac{d^4}{L}$$

using the equation $$\frac{d^4}{L} = \frac{256 \Delta Q T_{c1} P_s U_{Tc1} T_{c2} U_{Tc2}}{(\pi)(\rho_s)(T_s)[(P_1)^2 - (P_o)^2][(T_{c2})(U_{Tc2}) - (T_{c1})(U_{Tc1})]}$$

where

Q=column mass flow rate
$U_{TC}$=gas viscosity at specified column temperature
Tc=column temperature (Kelvin)
Ts=standard temperature (Kelvin)
Ps=Density of carrier gas at standard temperature and pressure
d=column internal diameter
L=column length
Pi=inlet pressure (PSIA)
Po=outlet pressure (PSIA)
Ps=standard ambient pressure (PSIA)
π3.141592654
Tc1=column temperature in step a
P1=column inlet head pressure in step a
Tc2=column temperature in steps (b) and (c)
P2&P3=column inlet head pressure in steps (b) and (c) respectively
(f) installing said ratio $$\frac{d^4}{L}$$

into said computer controlled chromatography system; and (g) perform chromatography runs employing said $$\frac{d^4}{L}$$

ratio in establishing column inlet pressures.

7. A gas chromatography system comprising:

(a) a computer including an input/output interface with an operator, a CPU and memory;
(b) an inlet gas mass flow controller;
(c) an electronic servo pressure controller;
(d) an oven and an oven temperature controller;
(e) a column and an injector, said column being mounted in said oven;
(f) means to detect and measure flow in said column;

THE IMPROVEMENT COMPRISING, (i) means for calibrating said column $$\frac{d^4}{L}$$

ratio, said means including means to establish at different temperatures either pressure at the head of said column or flow rate in said column and means to measure the corresponding flow rate or pressure, including means to employ measurements to compute said $$\frac{d^4}{L}$$

column calibration ratio;

(ii) means to store said $$\frac{d^4}{L}$$

column calibration ratio into said CPU memory;

(iii) means to cause said CPU to use said stored calibrated $$\frac{d^4}{L}$$

column calibration ratio and to calculate a pressure set-point proffie corresponding to a temperature profile input via said input/output interface; and (iv) said CPU being programmed to control said injection, temperature controller, flow controller, injector and electronic servo pressure controller to carry out a chromatography run employing said computed pressure set-point profile.

8. The system of claim 7, wherein said CPU is programmed to compute said calibration factor $$\frac{d^4}{L}$$

by solving the equation:

$$\frac{d^4}{L} = \frac{256 \Delta Q T_{c1} P_s U_{Tc1} T_{c2} U_{Tc2}}{(\pi)(\rho_s)(T_s)[(P_1)^2 - (P_0)^2][(T_{c2})(U_{Tc2}) - (T_{c1})(U_{Tc1})]}$$

where

Q=column mass flow rate
$U_{tc}$=gas viscosity at specified column temperature
Tc=column temperature (Kelvin)
Ts=standard temperature (Kelvin)
Ps=Density of carrier gas at standard temperature and pressure
d=column internal diameter
L=column length
Pi=inlet pressure (PSIA)
Po=outlet pressure (PSIA)
Ps=standard ambient pressure (PSIA)
π=3.14 1592654
Tc1=column temperature in first set of points
P1=column inlet head pressure
Tc2=column temperature in second set of points
ΔQ=flow rate difference between first and second points.

* * * * *